United States Patent
Sinderby

(10) Patent No.: US 8,551,009 B2
(45) Date of Patent: Oct. 8, 2013

(54) METHOD AND SYSTEM FOR DETERMINING DYNAMICALLY RESPIRATORY FEATURES IN SPONTANEOUSLY BREATHING PATIENTS RECEIVING MECHANICAL VENTILATORY ASSIST

(75) Inventor: Christer Sinderby, Toronto (CA)

(73) Assignee: Maquet Critical Care AB, Solna (SE)

( * ) Notice: Subject to any disclaimer, the term of this patent is extended or adjusted under 35 U.S.C. 154(b) by 786 days.

(21) Appl. No.: 12/161,373

(22) PCT Filed: Jan. 19, 2007

(86) PCT No.: PCT/CA2007/000079
§ 371 (c)(1),
(2), (4) Date: Aug. 8, 2009

(87) PCT Pub. No.: WO2007/082384
PCT Pub. Date: Jul. 26, 2007

(65) Prior Publication Data
US 2010/0228142 A1    Sep. 9, 2010

Related U.S. Application Data

(60) Provisional application No. 60/759,977, filed on Jan. 19, 2006.

(51) Int. Cl.
*A61B 5/085* (2006.01)
(52) U.S. Cl.
USPC ........................ 600/533; 600/529; 128/204.23
(58) Field of Classification Search
USPC .............................. 600/529–543; 128/204.23
See application file for complete search history.

(56) References Cited

U.S. PATENT DOCUMENTS

| 5,535,738 | A | | 7/1996 | Estes et al. |
| 5,671,752 | A | | 9/1997 | Sindreby et al. |
| 5,820,560 | A | * | 10/1998 | Sinderby et al. ............ 600/546 |

(Continued)

FOREIGN PATENT DOCUMENTS

| EP | 0 521 515 | 1/1993 |
| EP | 1 103 279 | 5/2001 |

(Continued)

OTHER PUBLICATIONS

"Lung Resistance and Elastance in Spontaneously Breathing Preterm Infants: Effects of Breathing Pattern and Demographics". Pandit et al. J Appl Physiol 88:997-1005, 2000.*

(Continued)

*Primary Examiner* — Navin Natnithithadha
*Assistant Examiner* — Meredith Weare
(74) *Attorney, Agent, or Firm* — Fay Kaplun & Marcin, LLP

(57) ABSTRACT

A method for determining dynamically a respiratory feature in a spontaneously breathing patient receiving mechanical ventilatory assist comprises: modifying a level of mechanical ventilatory assist to the patient, measuring an airway pressure, detecting a change of gradient of the measured airway pressure and determining the respiratory feature based on the measured airway pressure upon detecting the change of gradient of the airway pressure. Furthermore, the method also comprises: measuring a respiratory neural drive of the patient and detecting a lowest level of the measured respiratory neural drive for determining the respiratory feature based on the detected lowest level of respiratory neural drive.

57 Claims, 12 Drawing Sheets

(56) References Cited

U.S. PATENT DOCUMENTS

| | | | | |
|---|---|---|---|---|
| 5,884,622 | A | * | 3/1999 | Younes .................. 128/204.21 |
| 5,937,854 | A | | 8/1999 | Stenzler |
| 6,015,388 | A | * | 1/2000 | Sackner et al. ............... 600/529 |
| 6,257,234 | B1 | * | 7/2001 | Sun ......................... 128/204.18 |
| 6,588,423 | B1 | | 7/2003 | Sindreby |
| 2003/0078512 | A1 | * | 4/2003 | Jonson ......................... 600/538 |
| 2005/0005936 | A1 | | 1/2005 | Wondka |
| 2005/0211246 | A1 | * | 9/2005 | Beck et al. ............... 128/204.23 |
| 2005/0284476 | A1 | | 12/2005 | Blanch et al. |
| 2006/0060190 | A1 | * | 3/2006 | Sinderby ................. 128/200.14 |

FOREIGN PATENT DOCUMENTS

| | | |
|---|---|---|
| EP | 1 204 439 | 5/2002 |
| EP | 1 295 620 | 3/2003 |
| JP | 5 015 516 | 1/1993 |
| WO | 97/22377 | 6/1997 |
| WO | 2004/019766 | 3/2004 |
| WO | 2005/077268 | 8/2005 |
| WO | 2005/092189 | 10/2005 |

OTHER PUBLICATIONS

"New Modes of Mechanical Ventilation: Proportional Assist Ventilation, Neurally Adjusted Ventilatory Assist, and Fractal Ventilation". Navalesi et al. Curr Opin Crit Care 9:51-58. 2003.*

"A Method for Measuring Passive Elastance during Proportional Assist Ventilation". Younes et al. Am J Respir Crit Care Med vol. 164. pp. 50-60, 2001.*

"Mechanical Loading and Control of Breathing in Patients with Severe Chronic Obstructive Pulmonary Disease". Duranti et al. Thorax 1995;50:127-133.*

"Patient-Ventilator Interaction". Kondili et al. British Journal of Anaesthesia 91 (1): 106±19 (2003).*

"Respiratory Mechanics by Least Squares Fitting in Mechanically Ventilated Patients: Applications during Paralysis and during Pressure Support Ventilation." Iotti et al. Intensive Care Med (1995) 21:406-413.*

"Obstructive and Resistive Lung Mechanics." Waechter, Jason. Apr. 2005. http://www.teachingmedicine.com/pdf_files/Obstructive_Restrictive_2005.pdf.*

"Pressure Support Ventilation (PSV)." The Free Dictionary, Medical Dictionary. http://medical-dictionary.thefreedictionary.com/pressure+support+ventilation.*

"Respiratory Glossary." http://hydranencephaly.com/health%20conditions/respiratoryglossary.htm.*

"Respiratory Glossary." Sep. 21, 2007. http://hydranencephaly.com/health%20conditions/respiratoryglossary.htm.*

"Pressure Support Ventilation (PSV)." The Free Dictionary, Medical Dictionary. 2009. http://medical-dictionary.thefreedictionary.com/pressure+support+ventilation.*

Sinderby, "Neurally Adjusted Ventilatory Assist (NAVA)", Minerva Anestesiologica, vol. 68, No. 5, May 1, 2002, XP008102662, ISSN: 0375-9393, pp. 378-380.

Younes et al., "A Model for the Relation Between Respiratory Neural and Mechanical Outputs, I. Theory", Journal of Applied Physiology, American Physiological Soceity, US, vol. 51, No. 4, Jan. 1, 1981, XP009051921, ISSN: 8750-7587, pp. 963-978.

Sinderby et al., "Inspiratory Muscle Unloading by Neurally Adjusted Ventilatory Assist During Maximal Inspirator Efforts in Healthy Subjects", Chest, vol. 131, No. 3, Mar. 2007, pp. 711-717.

* cited by examiner

US 8,551,009 B2

METHOD AND SYSTEM FOR DETERMINING DYNAMICALLY RESPIRATORY FEATURES IN SPONTANEOUSLY BREATHING PATIENTS RECEIVING MECHANICAL VENTILATORY ASSIST

PRIORITY CLAIM

This application is a National Phase application of PCT Application Serial No. PCT/CA2007/000079 filed on Jan. 19, 2007; which claims the priority to the U.S. Provisional Application Serial No. 60/759,977 filed on Jan. 19, 2006. The specification of the above-identified application is incorporated herewith by reference.

FIELD OF THE INVENTION

The present invention relates to mechanical ventilatory assist. More specifically, but not exclusively, the present invention is concerned with a method and system for determining dynamically respiratory features in spontaneously breathing patients receiving mechanical ventilatory assist.

BACKGROUND OF THE INVENTION

First, a brief introduction about how inspiration occurs and how a ventilatory assist affects lung expansion will be provided.

Inspired lung volume or inflation of lungs is determined by the pressure distending the lungs, which is called the transpulmonary pressure $P_{TR}$, and the mechanical properties of the lung, such as elastance and resistance of the lung. $P_{TR}$ is generated by the respiratory muscles, which through an outward action acts to expand the lungs. In respiratory failure, increased load or inspiratory muscle weakness results in an inability to adequately ventilate the lungs such that ventilation will become inefficient. In spontaneously breathing patients, addition of mechanical ventilation (artificial respiration) is used to aid the (presumably weak) respiratory muscles to overcome the increased inspiratory load. The level of ventilatory assist is currently determined rather arbitrarily with a major focus to restore adequate blood gases. In spontaneously breathing patients, the ventilatory assist level should be high enough to ensure that adequate ventilation can take place, however, one should avoid too high levels of ventilatory assist since this may result in disuse atrophy of the inspiratory muscles. There are currently no methods available to monitor and ensure that ventilatory assist levels are adequate.

Using a neurally controlled ventilator, that is a ventilator that responds to patients' neural effort in both time (triggering and termination of assist) and space (magnitude of assist) (as disclosed in U.S. Pat. No. 6,588,423 B1, granted to Sinderby et al. on Jul. 8, 2003, entitled "Method and Device responsive to Myoelectrical Activity for Triggering Ventilatory Support"), ventilatory assist is uniquely synchronized to patient effort and the mechanical ventilator could be considered as an additional artificial inspiratory breathing muscle under the influence of the brain's respiratory centers and neural respiratory feedback systems. Given the neural integration of such a system, it is not possible to set the assist or ventilation to too high values. Consequently, the system can unload muscles, improve ventilation to levels that are preferred by the patient's respiratory centers. However, a neurally controlled ventilator system resists "over assist" of the patient. Therefore, muscle unloading only takes place by overcoming inertia, elastic and resistive loads. Unlike the conventional systems ("not neurally controlled in time and space"), it is not possible to hyperventilate to very low breathing frequencies or apnea, such that the respiratory drive and respiratory muscle activity, due to chemo receptor influence, will always persist (by Sinderby et al., Chest 2007 In Press).

In unhealthy lungs, some air sacs may collapse, meaning that in those collapsed sacs, gas cannot enter or leave them, thus preventing gas exchange through the collapsed air sacs; in this case, a ventilator will supply a higher concentration of oxygen in order to provide proper blood oxygenation. Also, a ventilator can supply positive end-expirtory pressure (PEEP) to recruit or maintain airways open.

During the inflation process of the lungs, by increasing the transpulmonary pressure $P_{TR}$, the collapsed air sacs will start to open up. When the collapsed air sacs start to open up, they are said to be recruited and the pressure at which the recruitment happens is called the critical opening pressure. However, continuing to increase the transpulmonary pressure $P_{TR}$ will lead to overinflation, which can be dangerous for the patient since it may cause lesions in the lung tissues, which will lead to air leakage out of the lung.

Furthermore, underinflation may also cause problems, such as atelectasis, when the recruited air sacs are de-recruited at a pressure threshold referred to as the critical closing pressure. Therefore, proper pressure provided by the mechanical ventilator should fall inside the thresholds of overinflation and underinflation pressures. In U.S. Pat. No. 5,937,854, granted to Alex Stenzler, on Aug. 17, 1999 and entitled "Ventilator Pressure Optimization Method and Apparatus", a method and apparatus for controlling the ventilation pressure are disclosed. By increasing incrementally the pressure, the lung volume is measured and then compared to a previous volume measure. If the increase in the lung volume is higher than 20% when compared to the past value, then the critical opening pressure has been reached. Therefore, the ventilatory apparatus will stop increasing the pressure. To measure the critical closing pressure, the pressure in the lungs is decrementally decreased and, at each decremental decrease, the lung volume is measured and then compared to the previous value. If a change in the volume of more than 20% is observed, then it means that the critical closing pressure has been reached. And the mechanical ventilatory assist machine stops decreasing the pressure. This method presents the drawback of depending on very slow inflations to measure a static pressure.

In Patent Application EP 1 295 620 A1, published on Mar. 26, 2003, by J. Björn, and entitled "A Method for Examining Pulmonary Mechanics and a Breathing Apparatus System", a method and apparatus for examining the pulmonary mechanics in a respiratory system is disclosed. More specifically, the apparatus determines a flow, volume and pressure of the gas streaming through the respiratory system. Furthermore, the apparatus compares the measured/determined flow, volume and pressure with reference values set by an operator and then produces an error signal for adjusting accordingly the apparatus. This method depends on oscillations in patients who are not breathing spontaneously.

In Patent Application EP 1 204 439 A1, published on May 15, 2002, by C. Sinderby, and entitled "Target Drive Ventilation Gain Controller and Method", a device for adjusting the degree of inspiratory assist, in relation to the patient's respiratory drive, representing a real need of the patient, is disclosed. This device first detects a signal representative of a respiratory drive, then compares this signal to a target drive and finally adjusts the gain of a controller of a lung ventilator in order to control the lung ventilator in relation to the respiratory drive. However, such a method of controlling inspiratory proportional pressure assist ventilation requires no knowledge of the mechanics of the lung, such as its elastance and resistance.

Therefore, until now, no dynamic measurements of the mechanics of the lungs have been proposed, using a respiratory neural drive for controlling a ventilator assist.

OBJECTS OF THE INVENTION

An object of the present invention is therefore to provide a method and device for determining dynamically respiratory features in spontaneously breathing patients receiving mechanical ventilatory assist.

SUMMARY OF THE INVENTION

More specifically, in accordance with the present invention, there is provided a method for determining dynamically a respiratory feature in a spontaneously breathing patient receiving mechanical ventilatory assist. The method comprises: modifying a level of mechanical ventilatory assist to the patient, measuring an airway pressure, detecting a change of gradient of the measured airway pressure and determining the respiratory feature based on the measured airway pressure upon detecting the change of gradient of the airway pressure.

The present invention further relates to a method for determining dynamically a respiratory feature in a spontaneously breathing patient receiving mechanical ventilatory assist. The method comprises: modifying a level of mechanical ventilatory assist to the patient, measuring a respiratory neural drive of the patient, detecting a lowest level of the measured respiratory neural drive and determining the respiratory feature based on the detected lowest level of respiratory neural drive.

The present invention is also concerned with a device for determining dynamically a respiratory feature in a spontaneously breathing patient receiving mechanical ventilatory assist. The device comprises: a ventilator for applying mechanical ventilatory assist to the patient, a controller of the ventilator for modifying a level of mechanical ventilatory assist to the patient, an airway pressure detector for measuring an airway pressure and detecting a change of gradient of the measured airway pressure, and a calculator, connected to the airway pressure detector, for determining the respiratory feature based on the airway pressure measured upon detecting the change of gradient of the measured airway pressure.

The present invention still further relates to a device for determining a respiratory feature in a spontaneously breathing patient receiving mechanical ventilatory assist. The device comprises: a ventilator for applying mechanical ventilatory assist to the patient, a controller of the ventilator for modifying a level of mechanical ventilatory assist to the patient, a respiratory neural drive detector for measuring a respiratory neural drive and for detecting a lowest level of the measured respiratory neural drive, and a calculator for determining the respiratory feature based on the detected lowest level of respiratory neural drive.

The foregoing and other objects, advantages and features of the present invention will become more apparent upon reading of the following non-restrictive description of an illustrative embodiment thereof, given by way of example only with reference to the accompanying drawings.

DETAILED DESCRIPTION OF THE ILLUSTRATIVE EMBODIMENTS

Figure 1:
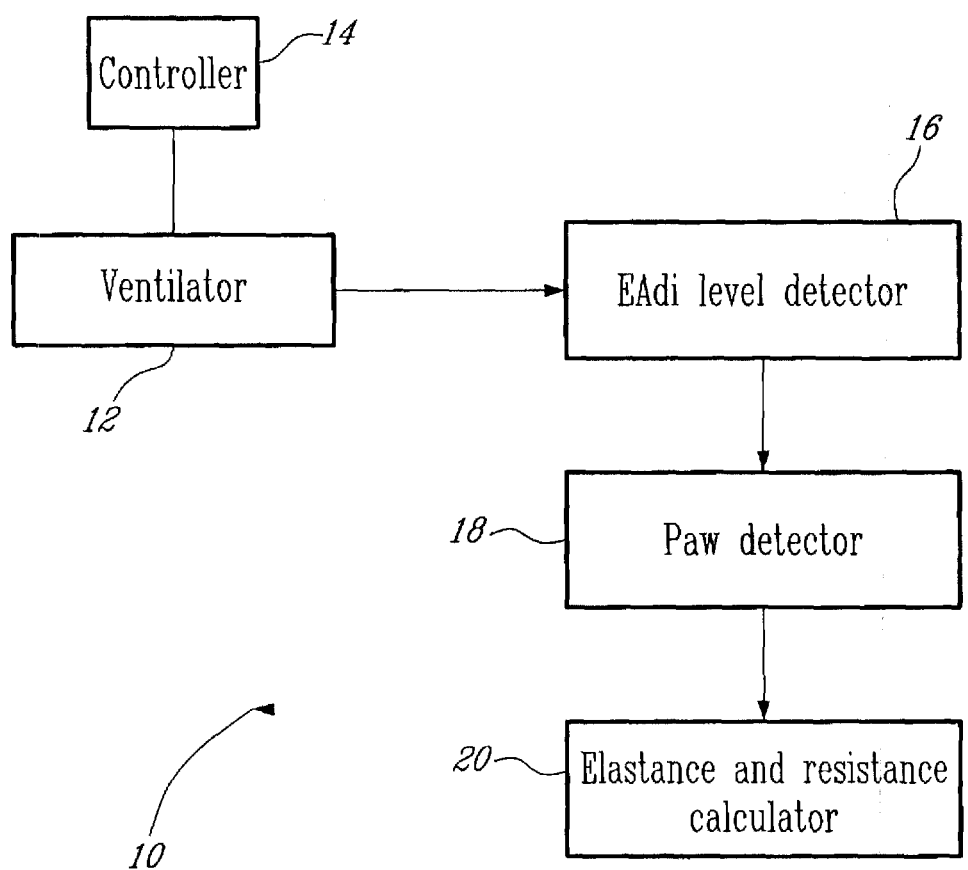
FIG. 1 is a schematic block diagram of a system for determining respiratory features according to the non-restrictive illustrative embodiment of the present invention.

Generally stated, the following description is concerned with a non-restrictive illustrative embodiment of the present invention for:

physiological determination of respiratory unloading, which corresponds to the determination of the range of applicable levels of respiratory assist from the level necessary to achieve the unloading of respiratory assist satisfying patients' respiratory demand, to the level that represents 100% of mechanical unloading of the respiratory muscles;

determination of respiratory lung mechanics;

determination of a level of positive end-expiratory pressure (PEEP) that is associated with the least impaired level of respiratory mechanics; and quantification of respiratory drive and partition of respiratory drive into chemical/habitual drive and load related drive;

in spontaneously breathing patients who receive mechanical ventilatory assist.

Furthermore, this non-restrictive illustrative embodiment according to the present invention also pertains to the measurements of:

respiratory drive; the respiratory drive can be obtained by measuring the diaphragm electrical activity EAdi as taught in U.S. Pat. No. 5,671,752, granted to C. Sinderby et al., on Sep. 30, 1997; this patent uses an array of electrodes to detect electromyographic signals of reverse polarities, to which a double subtraction technique is applied in view of obtaining signals with improved signal-to-noise ratio;

airway pressure $P_{aw}$; the airway pressure can be measured in the respiratory circuit ($P_{aw}$ can also be measured in the airways or in the mechanical ventilator); and inspiratory and expiratory flow and volume; these flow and volume can be measured in the respiratory circuit or in the mechanical ventilator;

in a patient who is breathing, for example, on a neurally controlled ventilator, which delivers pressure in proportion to the inspiratory activity or effort. This can be performed by, for example, using a mechanical ventilator controlled by neural drive (diaphragm electrical activity EAdi) as outlined in U.S. Pat. No. 5,820,560, granted to C. Sinderby et al., on Oct. 13, 1998, or using a mechanical ventilator that delivers ventilatory assist between the beginning and end of the diaphragm electrical activity EAdi as described in U.S. Pat. No. 6,588,423, granted to C. Sinderby, on Jul. 8, 2003.

As stated hereinabove, the transpulmonary pressure $P_{TR}$, which represents the pressure required for distending the lungs, is given by the difference between the airway pressure $P_{aw}$ and pleural pressures, the latter being usually measured through an esophageal balloon ($P_{ea}$). Thus, the transpulmonary pressure $P_{TR}$ equals the airway pressure $P_{aw}$ minus the pleural pressure, which is typically estimated by $P_{es}$, so that $P_{TR}=P_{aw}-P_{es}$. During a non-assisted inspiration (i.e. without a mechanical positive pressure ventilator for example), the lung distending pressure (i.e. the gradient of transpulmonary pressure acting to expand the lungs) is similar to $P_{as}$–atmospheric pressure, i.e. change in $P_{TR}$=change in $P_{es}$. If a positive pressure ventilator is applied to the airways, then the transpulmonary pressure $P_{TR}$ can be calculated from the difference $P_{aw}-P_{es}$.

Generally stated, the non-restrictive illustrative embodiment of the present invention is based on a progressive increase of ventilatory assist starting from a zero level (or small level) to a high level. The increase of assist is preferably linear but can also be arbitrary or follow a nonlinear function. When ventilatory assist from a mechanical ventilator is controlled using diaphragm electrical activity EAdi as outlined in U.S. Pat. No. 5,820,560, the ventilatory assist, which corresponds to the pressure $P_{aw}$ delivered to the patient, is obtained by multiplying the diaphragm electrical activity EAdi with a proportionality factor γ such that $P_{aw}=EAdi \bullet \gamma$. Hence, an increase of the proportionality factor γ when/if EAdi remains constant, increases the ventilatory assist (i.e. increases the pressure $P_{aw}$ in the respiratory circuit). If EAdi is decreasing when the proportionality factor γ is increased, then the rate at which $P_{aw}$ increases will decrease.

More specifically, FIG. 1 illustrates a system 10 according to the non-restrictive illustrative embodiment of the present invention. The system 10 comprises a mechanical ventilator 12, a controller 14, an EAdi level detector 16, a $P_{aw}$ detector 18 and an elastance and resistance calculator 20.

The ventilator 12 can be the mechanical ventilator disclosed in U.S. Pat. No. 5,820,560, whose ventilatory assist is controlled as a function of a respiratory neural drive such as EAdi (electrical activity of the diaphragm). Furthermore, the ventilator 12 is connected to the controller 14 for adjusting the degree of assist from the ventilator 12, through the above described proportionality factor γ. By increasing the proportionality factor γ, the degree of ventilatory assist is increased and vice versa if the proportionality factor γ is decreased.

When ventilatory assist is applied to a patient (not shown), the EAdi level detector 16, which is connected both to the patient and the ventilator 12, detects and records the EAdi level in response to ventilatory assist. The EAdi level detector 16 is further designed to detect a lowest level of EAdi, meaning that it can determine the point where the EAdi level reaches a plateau and the value of this plateau. From this level on, EAdi becomes insensitive to an increase of ventilatory assist, meaning that EAdi is no longer decreasing even though the level of assist may still be increasing. At this level of lowest EAdi, $P_{es}$ is close to zero, therefore $P_{aw}=P_{TR}$.

The $P_{aw}$ detector 18 is connected to the EAdi level detector 16. The $P_{aw}$ detector 18 detects a change in the gradient of the airway pressure $P_{aw}$ supplied by the ventilator 12. When a change in the gradient of $P_{aw}$ is detected, then it means that respiratory unloading has satisfied respiratory centers.

Once the lowest level of EAdi and a change in the gradient of $P_{aw}$ are determined, the mechanics of the lungs such as elastance and resistance can be calculated by the calculator 20.

Physiological Determination of Respiratory Unloading

Figure 2:
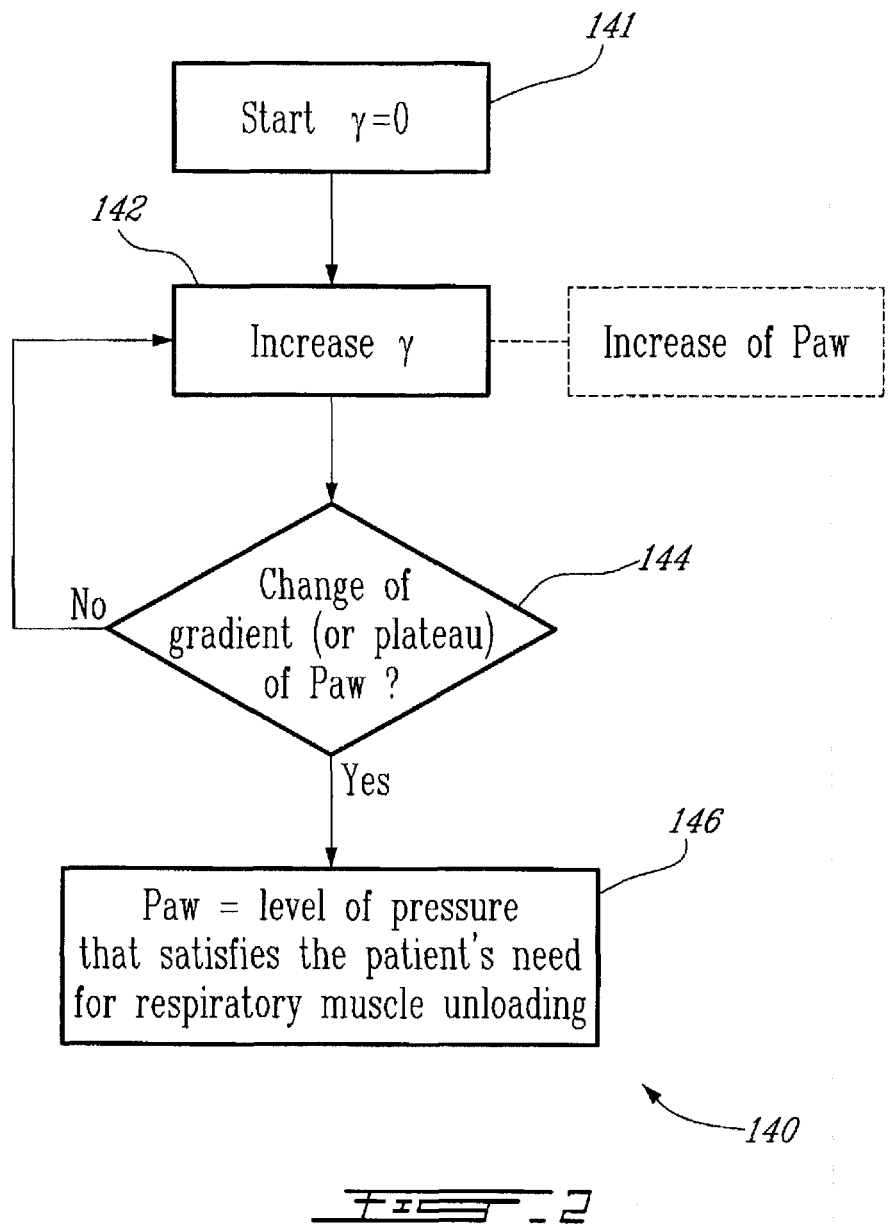
FIG. 2 is a flow chart illustrating a method of physiological determination of respiratory unloading according to the non-restrictive illustrative embodiment of the present invention.

Now, turning to FIG. 2, a method 140 for physiological determination of respiratory unloading is described, using the system 10 of FIG. 1.

At the beginning, the proportionality factor γ is set to a small value, in operation 141. It can be set to zero, for example.

In operation 142, the proportionality factor γ is then increased by a certain increment by the controller 14 of FIG. 1, or in a linear manner. The value and nature of the increment can depend on many factors such as the health of the patient and the category of the patient (infant, child, adult, etc.). As a consequence of the increase of the proportionality factor γ, the ventilatory assist also increases to a higher level. Therefore, there is an increase in $P_{aw}$ associated with increasing the proportionality factor γ.

At some point in time, corresponding to a certain level of increase of the proportionality factor γ, the rate of increase in $P_{aw}$ will slow down and/or reach a new gradient or plateau. Therefore, in operation 144, a change in the gradient of $P_{aw}$ is checked, through for example the $P_{aw}$ detector 18 of FIG. 1.

If no change in the gradient of $P_{aw}$ is detected, then the method 140 goes back to operation 142 for continuing to increase the proportionality factor γ through the controller 14 of FIG. 1.

If a change in the gradient of $P_{aw}$ is detected in operation 144, then $P_{aw}$ is measured and recorded in operation 146.

When the gradient of $P_{aw}$ changes, this indicates that the rate of decrease of EAdi has increased so as to reduce the increase of $P_{aw}$. This also suggests that the level of ventilatory assist satisfies the muscular receptors sensitive to muscle load and pulmonary receptors responsive to lung recruitment/stretch. The point where the rate of increase of $P_{aw}$ (gradient)

changes or reaches a plateau can be determined, for example, by visual inspection, or by algorithms for calculating the rate of increase of $P_{aw}$ or by applying trigonometric functions. Such functions can be implemented in the $P_{aw}$ detector 18.

Hence, the value of $P_{aw}$ and the proportionality factor γ observed at the point where the rate of increase of $P_{aw}$ (gradient) changes or reaches a plateau indicate a level of ventilatory assist that is likely to satisfy the patient's need for respiratory muscle unloading, as determined by the patient respiratory centers. It should be noted that repeated titrations would increase the reliability of the measurements of $P_{aw}$. Also, if the patient improves his/her respiratory function or capability of breathing by himself/herself, one would expect a lower level of $P_{aw}$ at the point where the rate of increase of $P_{aw}$ (gradient) changes or reaches a plateau and vice versa if the patient's respiratory function is deteriorated.

Figure 3:
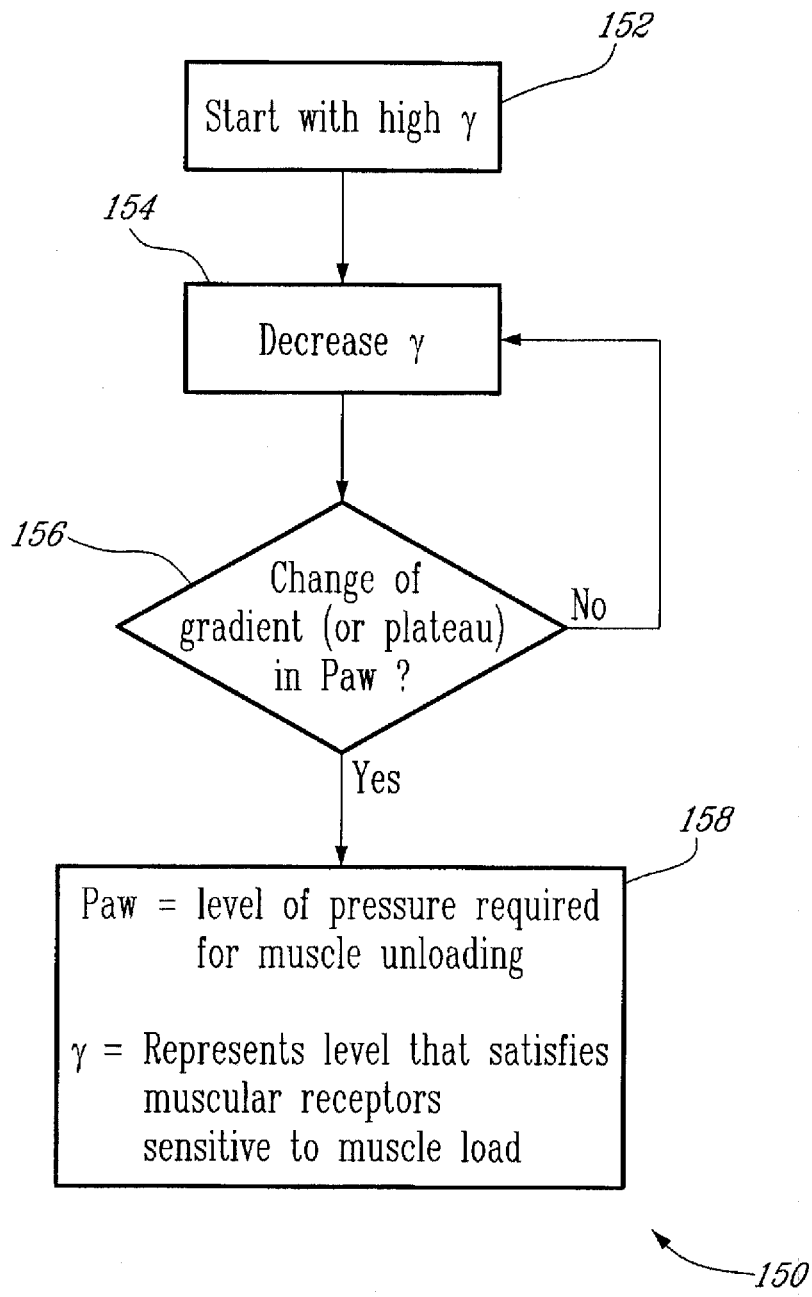
FIG. 3 is a flow chart illustrating an alternative method of physiological determination of respiratory unloading according to the non-restrictive illustrative embodiment of the present invention.

According to an alternative implementation of the non-restrictive embodiment of the present invention, the point where the rate of increase of $P_{aw}$ (gradient) changes or reaches a plateau can also be determined by starting with a high assist/high proportionality factor γ and then reducing the assist/proportionality factor γ until a change of gradient of $P_{aw}$ is observed. This alternative method 150 is illustrated in FIG. 3.

At the beginning, in operation 152, the proportionality factor γ is set to a high value. This value can be easily determined by a person of ordinary skill in the art and will depend on parameters such as the health of the patient and the patient's category (infant, child, adult, etc.).

Then, in operation 154, the proportionality factor γ is decreased, for example in a linear manner.

In operation 156, a change in the gradient of $P_{aw}$ is checked. If there is no change in the gradient of $P_{aw}$, then the method 150 goes back to operation 154 for continuing to decrease the proportionality factor γ.

If a change in the gradient of $P_{aw}$ occurs, then in operation 158, the current value of $P_{aw}$ is recorded and represents the level of pressure required for respiratory muscle unloading. Also, the current value of the proportionality factor γ is stored and represents the level of the proportionality factor γ that satisfies muscular receptory sensitive to muscle load (muscles no longer need to work).

Determination of Respiratory Lung Mechanics

Figure 4:
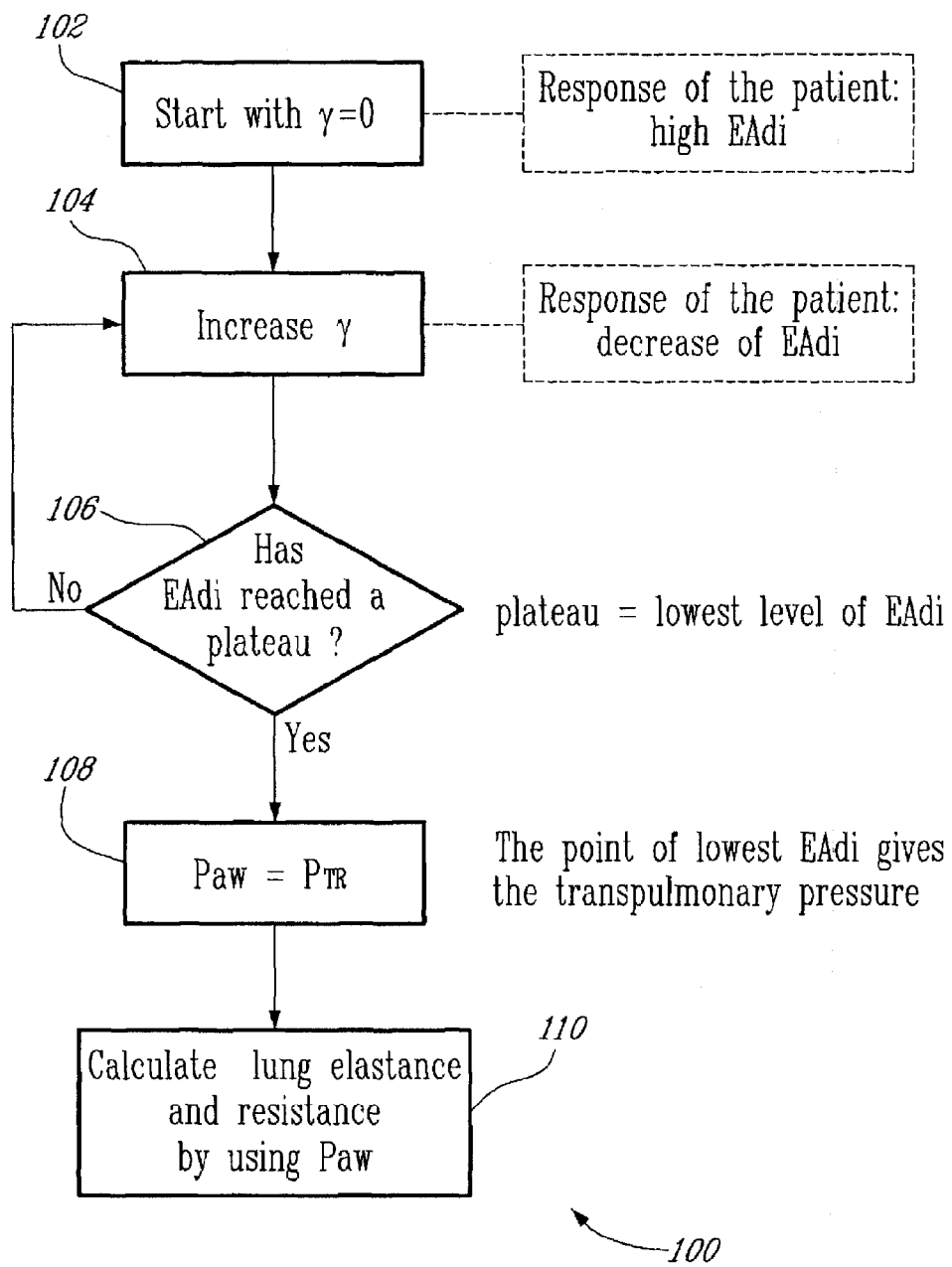
FIG. 4 is a flow chart illustrating a method for determining respiratory lung mechanics according to the non-restrictive illustrative embodiment of the present invention.

Now, turning to FIG. 4, a method 100 for determining the respiratory lung mechanics is described.

In accordance with the non-restrictive illustrative embodiment of the present invention, in operation 102, the method 100 starts with a low proportionality factor γ, for example, it can be set to zero (γ=0). In the case where γ=0, it means that no ventilatory assist is delivered to the patient. If the patient's response is normal, then an absence of assist will result in an increased/high respiratory drive and high level of diaphragm electrical activity (i.e. high level of EAdi).

The proportionality factor γ is then increased in operation 104, for example by a given increment or in a linear manner. In consequence, EAdi decreases as illustrated in the upper curve of FIG. 12. Furthermore, FIG. 12 shows an example of EAdi and $P_{aw}$ during titration with a linearly increasing proportionality factor γ starting from zero (0).

Figure 12:
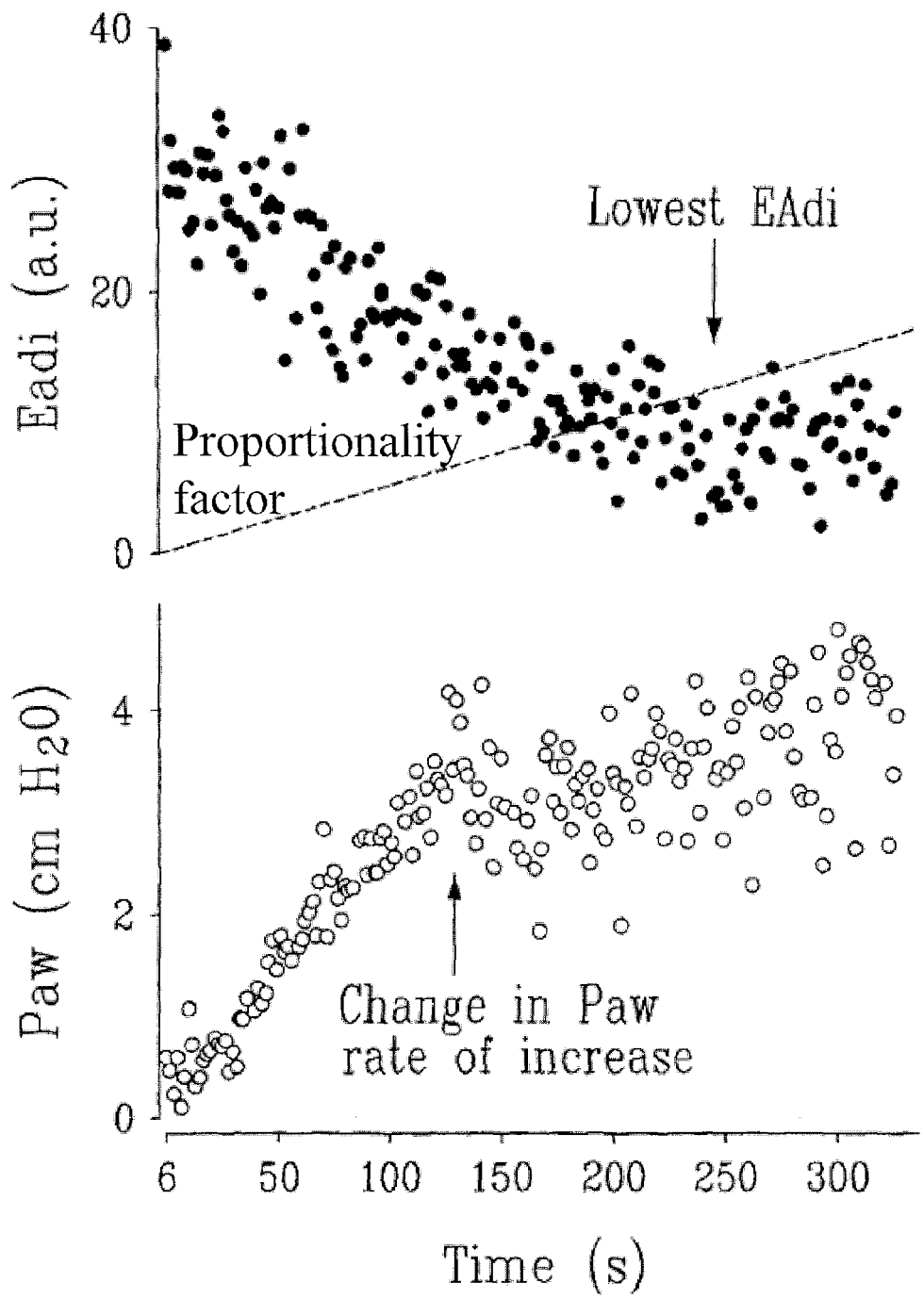
FIG. 12 is a graph showing an example of neurally controlled ventilator applied during acute respiratory failure, wherein a linearly increasing proportionality factor $\gamma$ from zero to a high level typically results in a rapid shallow breathing pattern at zero level of assist associated with high neural respiratory drive.

More specifically, as illustrated in FIG. 12, as the proportionality factor γ is increased, the airway pressure $P_{aw}$ will increase at a rate determined by the rate of increase of the proportionality factor γ and the EAdi response. Typically, the dynamics between these different variables are as follows: EAdi will first remain at a high level or slowly decrease, and $P_{aw}$ will increase at a relatively fast rate. At some point, EAdi will decrease at a more rapid rate, thus slowing the rate of increase in $P_{aw}$.

In operation 106, the EAdi level detector 16 (see FIG. 1) determines if the level of EAdi has reached a plateau or not.

If the level of EAdi has not reached a plateau yet, the method 100 goes back to operation 104 in order to continue to increase the proportionality factor γ. Indeed, continuing to increase the proportionality factor γ will at some point cause the neural drive EAdi to reach a lowest level of neural drive where it will plateau.

If the level of EAdi has reached a plateau, then in operation 108, a value for $P_{aw}$ is obtained. The point of lowest level of neural drive EAdi most likely represents the point where the respiratory work load is compensated as indicated by the abolished inspiratory $P_{es}$ in FIG. 7. In other words, the pressure required to inflate the lungs is provided via the mechanical ventilator.

The lowest level of the neural drive EAdi is determined at the point where EAdi stops to decrease, which is referred to as the lowest EAdi level in the present specification. This lowest EAdi level represents the case where the mechanical ventilatory assist replaces the inspiratory muscles' work to expand the lungs.

Hence, when the lowest EAdi level has been reached, in operation 108, the pressure delivered by the ventilator ($P_{aw}$) has eliminated the patient's own inspiratory pressure generation (i.e. the deflections in $P_{es}$ are close to zero) such that $P_{aw}$ represents the transpulmonary pressure $P_{TR}$ (i.e. the pressure for distending the lungs), so that $P_{aw}=P_{TR}$.

Figure 7:
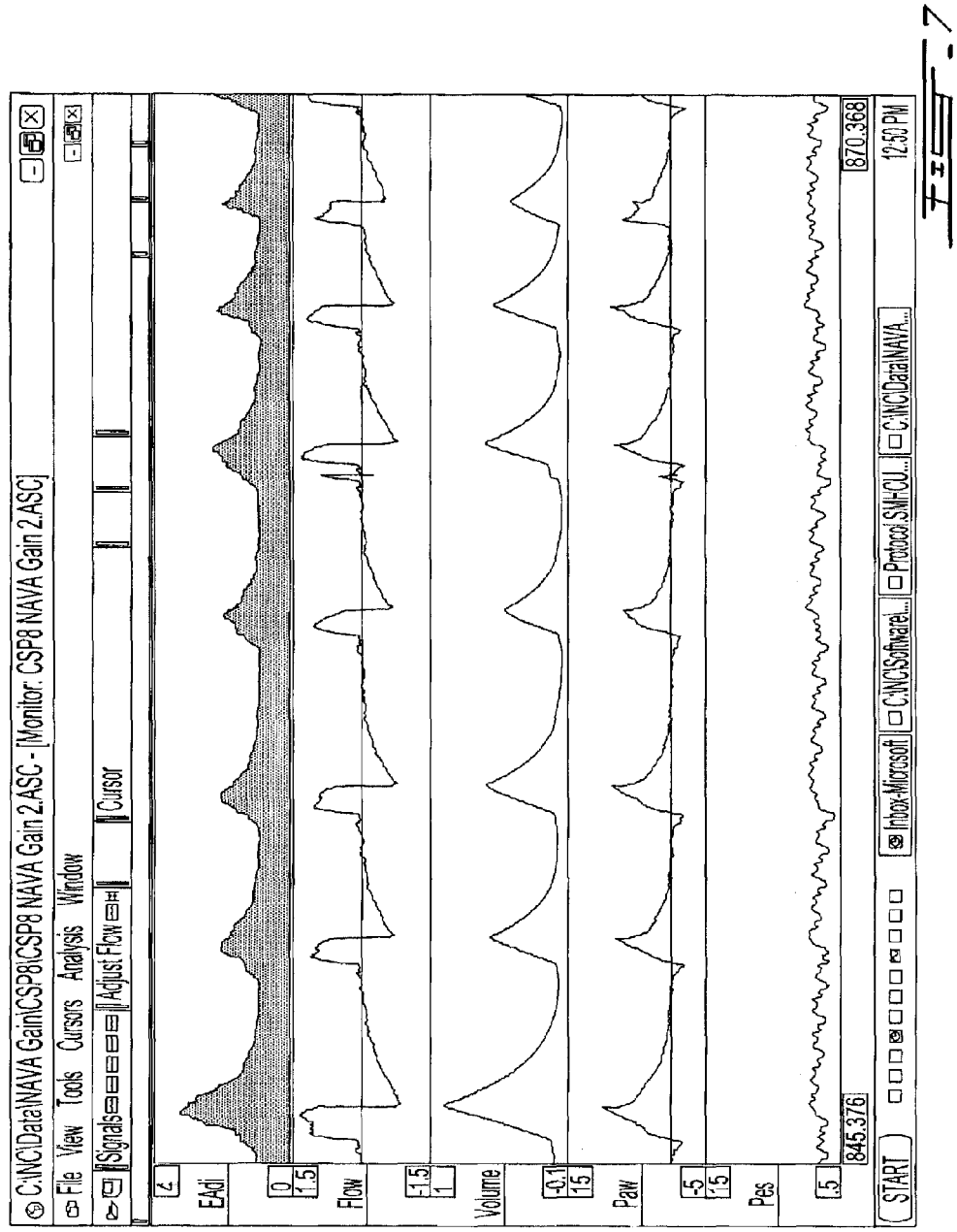
FIG. 7 is a graph illustrating an example of diaphragm electrical activity EAdi, flow, volume, airway pressure $P_{aw}$ and pleural pressure $P_{es}$ at a level where an increased proportionality factor $\gamma$ has reduced the neural drive EAdi to its lowest level.

FIG. 7 shows an example of curves corresponding to EAdi flow, volume, $P_{aw}$ and $P_{es}$ at the lowest EAdi level.

Given that inspired lung volume is determined by the transpulmonary pressure $P_{TR}$ and the mechanical properties of the lungs, it is possible to calculate the resistive and elastic mechanical properties of the lungs. Therefore, in operation 110, using $P_{aw}$, which is equal to the transpulmonary pressure $P_{TR}$ at the level of lowest EAdi, dynamic elastance and resistance of the lungs are calculated, through the calculator 20 of FIG. 1, for example.

Figure 8:
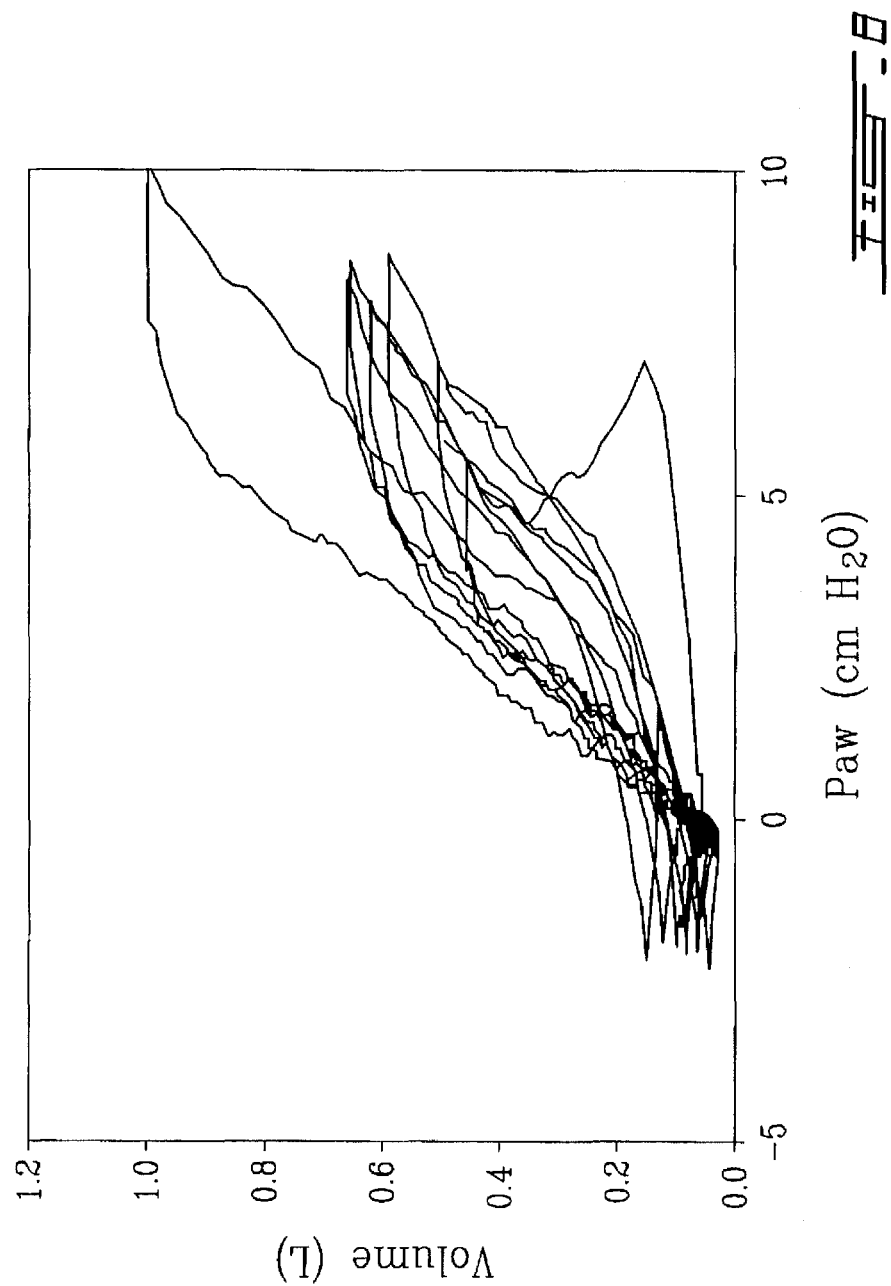
FIG. 8 is a graph showing an example of volume and airway pressure $P_{aw}$ curve for inspiration and expiration obtained at the level where the increased proportionality factor $\gamma$ has reduced neural drive EAdi to its lowest level.
Figure 11:
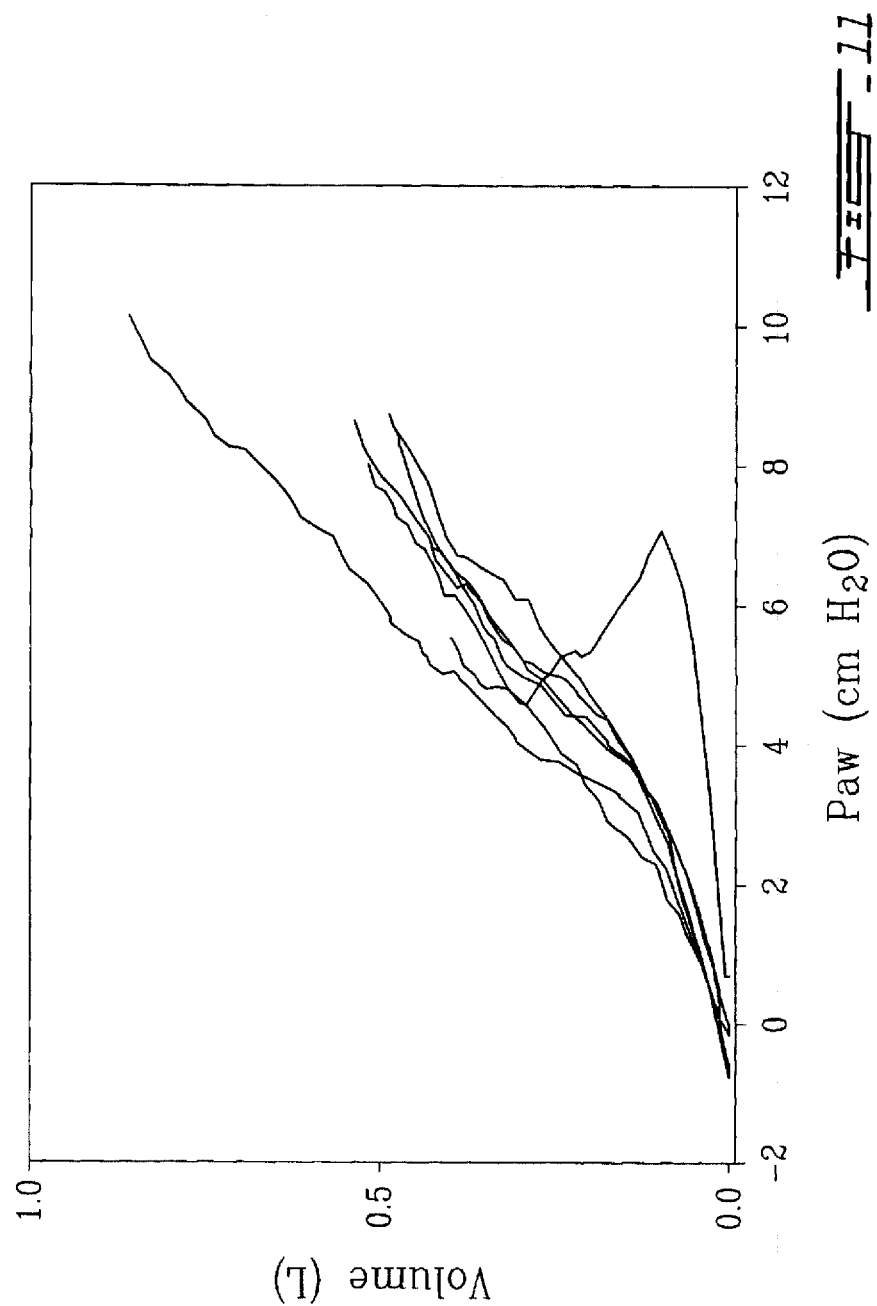
FIG. 11 is a graph showing an example of volume and airway pressure $P_{aw}$ curve for inspiration obtained at the level where the increased proportionality factor $\gamma$ has reduced neural drive EAdi to its lowest level.

As a non-limitative example, to determine dynamic elastance of the lungs, volume and transpulmonary pressure $P_{TR}$ can be used. An example of curves of the volume in function of $P_{aw}$ is illustrated in FIGS. 8 and 11. It should be noted that the same curves as those in FIG. 11 can also be obtained for only expiration to determine expiratory mechanics.

Figure 9:
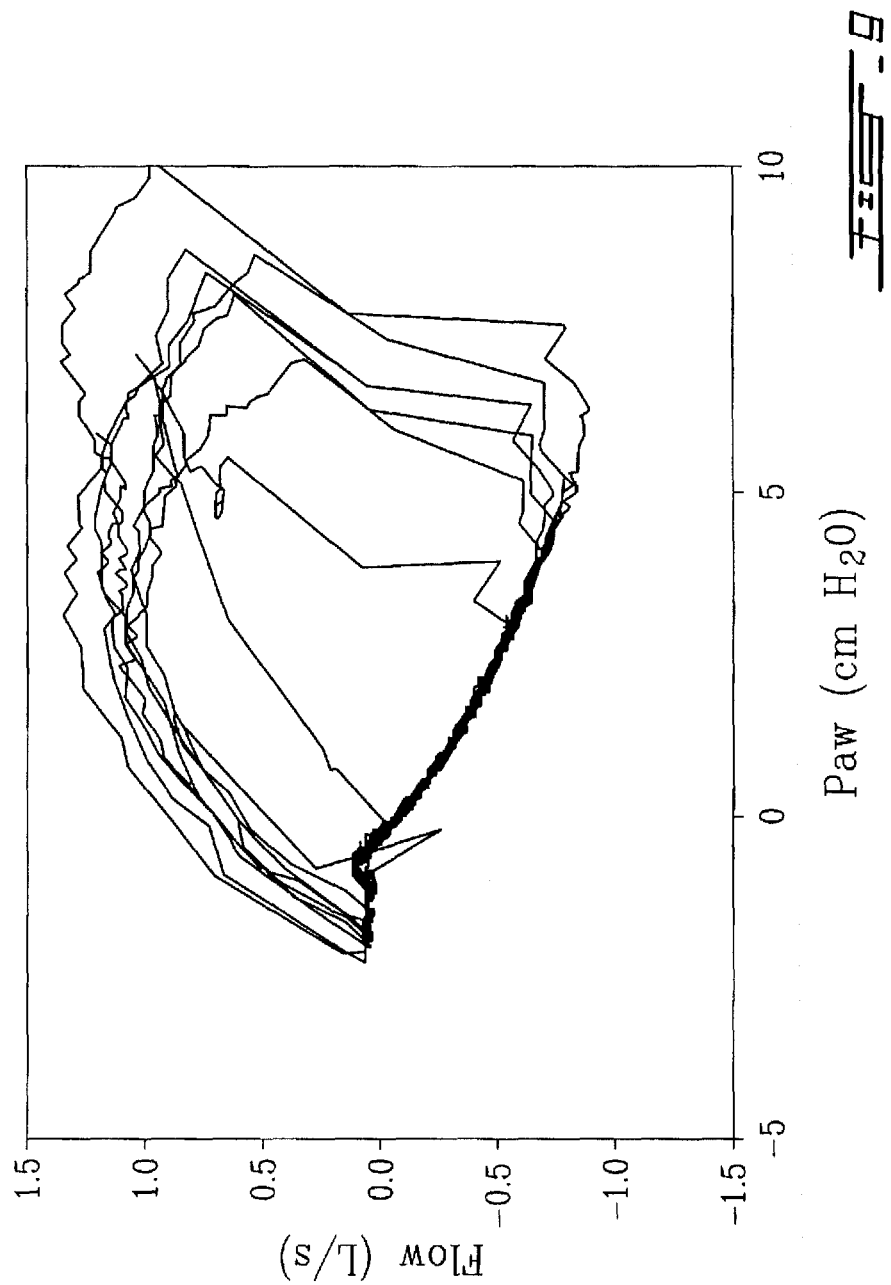
FIG. 9 is a graph showing an example of flow and airway pressure $P_{aw}$ curve for inspiration and expiration obtained at the level where the increased proportionality factor $\gamma$ has reduced neural drive EAdi to its lowest level.
Figure 10:
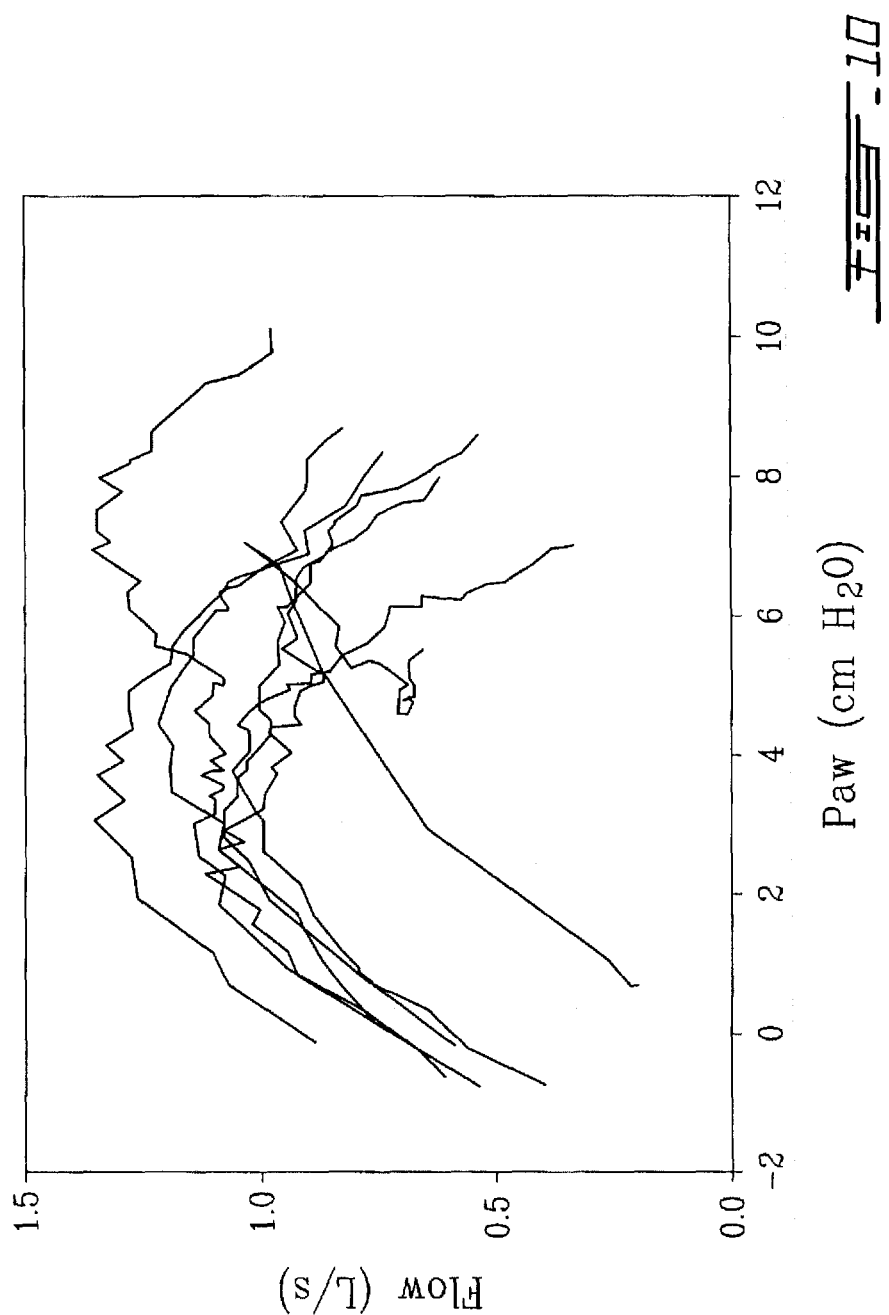
FIG. 10 is a graph showing an example of flow and airway pressure $P_{aw}$ curve for inspiration obtained at the level where the increased proportionality factor $\gamma$ has reduced neural drive EAdi to its lowest level.

To determine dynamic resistance of the lungs, flow and transpulmonary pressure $P_{TR}$ can be used. An example of curves of the flow in function of $P_{aw}$ is illustrated in FIGS. 9 and 10. It should be noted that the same curves as those in FIG. 10 can also be obtained for only expiration to determine expiratory mechanics.

Several methods can be used to calculate lung elastance (or compliance) and resistance. They can be implemented in the calculator 20 of FIG. 1.

For example, elastance can be estimated by measuring the inspiratory transpulmonary pressure swing and the corresponding lung volume during an inspiration and then calculate the pressure to volume ratio. Inspiratory resistance can be obtained by calculating a ratio between the inspiratory transpulmonary pressure swing and the flow rate during, for example, mid-inspiratory volume of an inspiration.

Another example for calculating lung elastance consists of applying a multiple linear regression analysis using the transpulmonary pressure $P_{TR}$ as the dependent variable and flow and volume as the independent variables; regression coefficients for flow and volume can then be determined. Hence, it is possible to calculate the amount of pressure necessary to generate a given volume and obtain a value representative of elastic properties of the lungs or calculate how much volume is obtained for a given transpulmonary pressure $P_{TR}$ (i.e. the compliance of the lungs). From the same regression analysis, it is also possible to calculate the amount of transpulmonary pressure $P_{TR}$ necessary to generate a given flow (i.e. resistive components of the lungs).

Since the pleural/esophageal pressures are negligible when the assist level has been increased to the level where the lowest EAdi level is reached, $P_{aw}$ is then similar to the transpulmonary pressure $P_{TR}$ at the lowest EAdi level. Therefore, $P_{aw}$ can be used to calculate the lung mechanics in operation 110.

It should be noted that once it is confirmed that the level of EAdi has reached its lowest level, the titration should be discontinued in order to avoid over-assist.

Determination of Level of Positive End-Expiratory Pressure (Peep) that is Associated With the Least Impaired Level of Respiratory Mechanics Based on the results obtained by using the methods 140, 150 and 100 as described in FIG. 2, 3 or 4, variable determination, such as elastance and resistance of the lungs can then be determined for different levels of PEEP, as will be described hereinbelow. Indeed, the lowest level of EAdi and the value of $P_{aw}$ at the point when its gradient changes allow for dynamic measurements.

Figure 5:
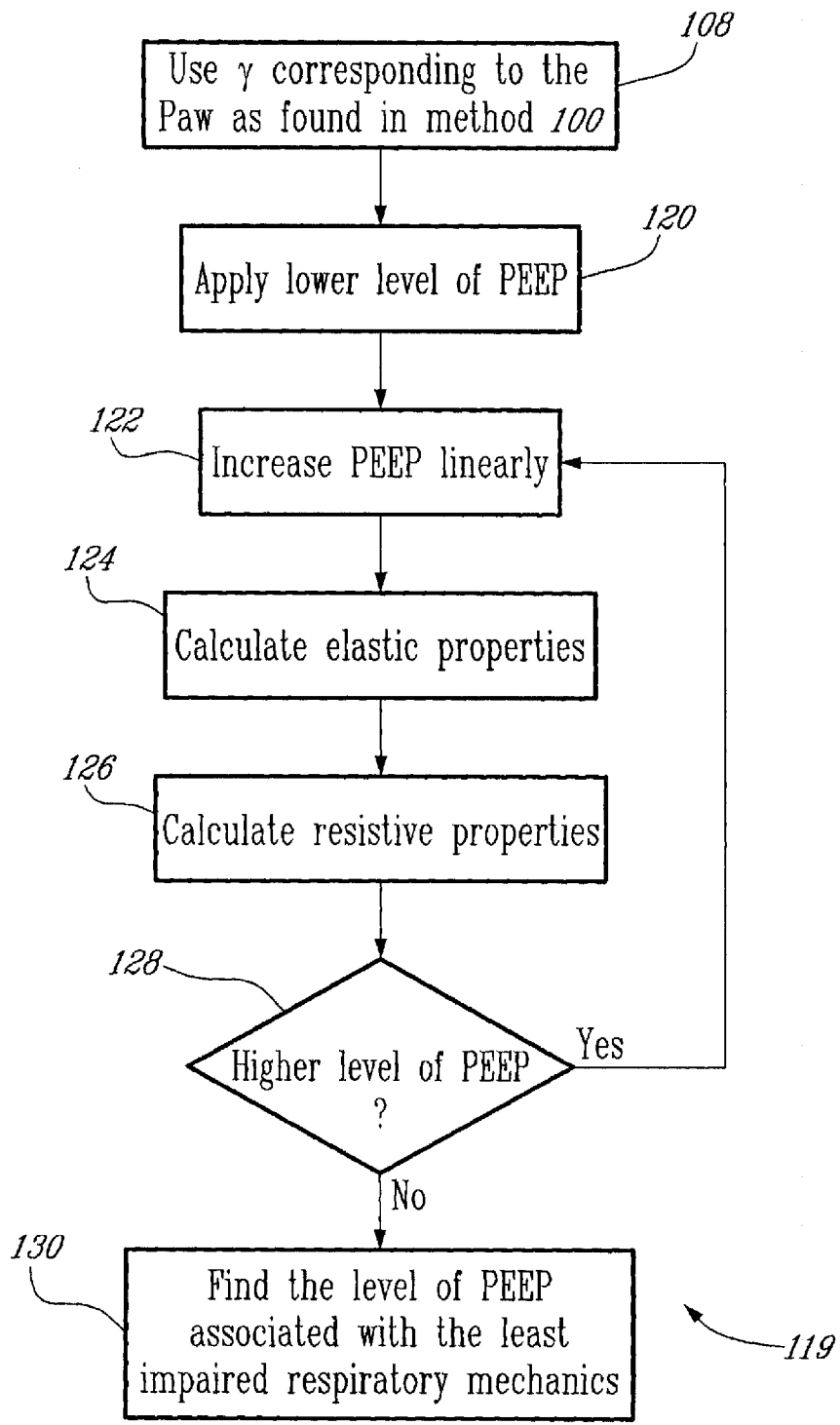
FIG. 5 is a flow chart illustrating a method for determining a level of PEEP associated with the least impaired level of respiratory mechanics according to the non-restrictive illustrative embodiment of the present invention.

Now, referring to FIG. 5, a method 119 for determining a level of PEEP associated to the least impaired level of respiratory mechanics is described.

At the level of ventilatory assist representative of the lowest EAdi level, different levels of positive end-expiratory pressure (PEEP) can be applied through an expiratory valve (not shown) for example. Increasing PEEP acts such as to distend the lungs and is clinically used to keep the airways open (i.e. to avoid lung collapse/atelectasis). If the lungs collapse, then more transpulmonary pressure $P_{TR}$ is required during each inspiration since the collapsed airways need to open up. This will, for example, increase the dynamic elastance of the lungs, and thus the lungs are less compliant.

If PEEP is applied to a level that prevents collapse of the airways, then less transpulmonary pressure $P_{TR}$ will be needed to generate a given inspiratory volume i.e. the elastance of the lungs is increased (the lungs are more compliant).

If the PEEP level is further increased, the further expansion of the lungs will make the lungs stiffer such that more pressure will be needed to generate a given inspiratory volume, and thus the lungs are less compliant.

By applying PEEP at various levels, at the level of ventilatory assist that represents the lowest EAdi level, the elastic and resistive properties of the lungs can be dynamically determined as described above for each level of PEEP applied.

Therefore, the method 119 of FIG. 5 starts by applying a PEEP of lower level, for example, through an expiratory valve (not shown), in operation 120, at the level of ventilatory assist (pressure $P_{aw}$) representative of the lowest EAdi level found in operation 108 of FIG. 4, by using the corresponding value of the proportionality factor γ.

Then the level of PEEP is increased, for example, linearly, in operation 122.

In operation 124, for the level of PEEP as determined in operation 122, the elastic properties of the lungs are calculated, using methods well known to those of ordinary skill in the art and using the calculator 20 of FIG. 1, for example. This value of the PEEP is recorded.

In operation 126, for the same level of applied PEEP, the dynamic resistive properties of the lungs are calculated, using methods well known to those of ordinary skill in the art and using the calculator 20 of FIG. 1, for example. This value of the PEEP is recorded.

Then, in operation 128, it is checked to see if the level of applied PEEP has reached a higher level, which can be determined by a clinician or a person of ordinary skill in the art, according to the needs of each patient.

If the level of applied PEEP has not reached yet the higher level, then the method 119 goes back to operation 122 in order to continue to increase, for example, linearly, the level of PEEP to an increased level and then to calculate the dynamic elastic and resistive properties of the lungs (respectively operations 124 and 126).

If the level of PEEP has already reached the higher level of operation 128, then, in operation 130, it is possible to determine which level of PEEP, among the different increased levels of PEEP, is associated with the least impaired respiratory mechanics by comparing the different calculated values of elastic and resistive properties. In other words, by comparing elastance and resistance values at various levels of PEEP at the level of ventilatory assist that represents the lowest EAdi level, one can determine which PEEP level is associated with the lowest level of elastic and resistive loads. Generally, the level of PEEP associated with the lowest elastic and resistive loads is the one that is most likely related to ideal lung recruitment.

Figure 6:
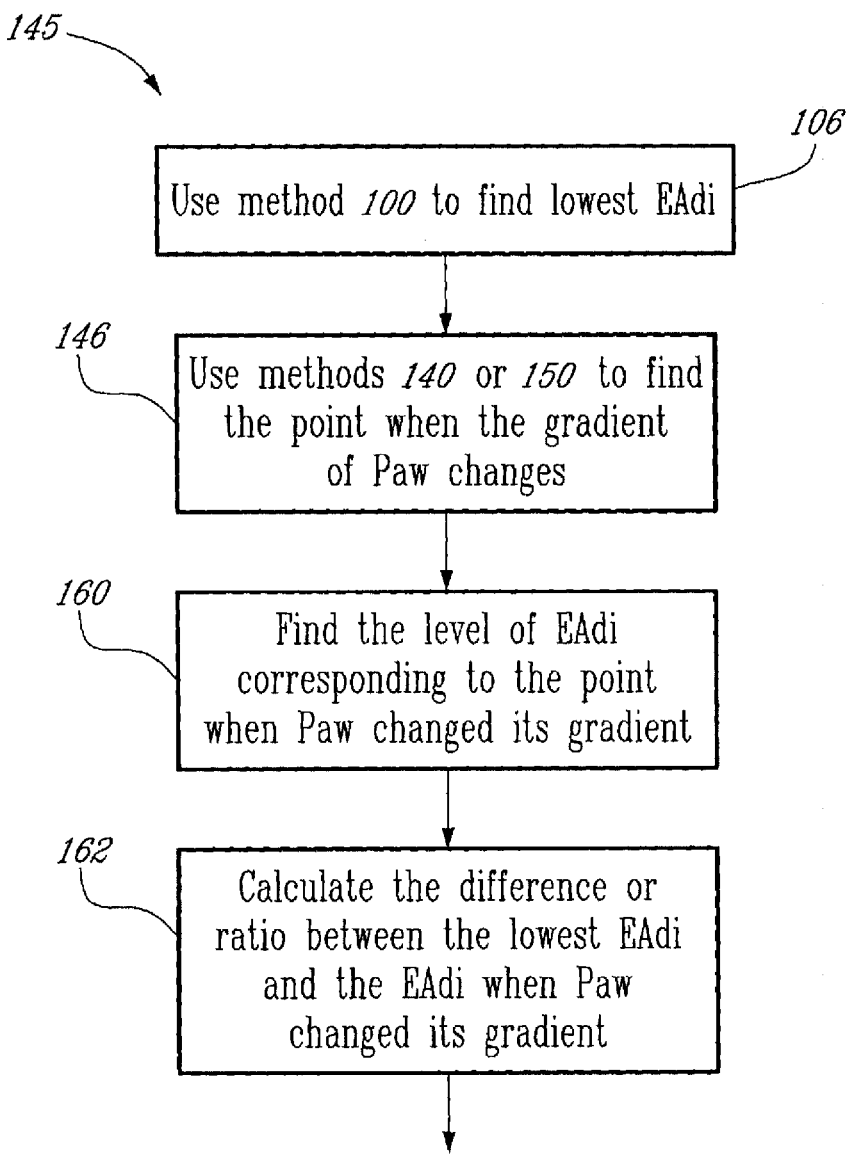
FIG. 6 is a flow chart illustrating a method for quantifying respiratory drive and partitioning the respiratory drive into chemical/habitual drive and load related drive.

Quantification of Respiratory Drive and Partition of the Respiratory Drive into Chemical/Habitual Drive and Load Related Drive Referring now to the flow chart in FIG. 6, a method 145 for quantifying a respiratory drive is described.

As stated before, since the lowest EAdi level that can be reached with increasing levels of assist/proportionality factor γ corresponds to a level where the lung distending pressure generated by the patient is eliminated, the pressure delivered by the ventilator ($P_{aw}$) then represents the transpulmonary pressure $P_{TR}$ (i.e. the pressure distending the lungs). Hence, the mechanical load necessary to inflate the lungs is abolished and one can assume that the respiratory drive at this level of ventilatory assist is little affected by respiratory load or respiratory muscle weakness but mainly influenced by metabolism, blood gases, and patients comfort level and similar variables.

Moreover, it is assumed that the point where the rate of increase in $P_{aw}$ (gradient) changes or reaches a plateau represents the level of assist/proportionality factor γ that satisfies muscular receptors sensitive to muscle load and pulmonary receptors responsive to lung recruitment/stretch.

Hence, by calculating a difference or ratio in EAdi between the point of lowest level of EAdi and the point where the rate of increase in $P_{aw}$ (gradient) changes or reaches a plateau, the amount of respectively absolute or relative increase in EAdi contributed by the respiratory mechanical load is determined.

It should be noted that breathing frequency and tidal volume do normally not change between these points.

More specifically, the method 145 is based on the lowest EAdi level determined in operation 106, in the method 100 of FIG. 4. The method 145 also uses the value of $P_{aw}$ determined in operation 146 of the method 140 of FIG. 2 or in operation 158 of the method 150 of FIG. 2 when its gradient changes.

In operation 160, a level of EAdi corresponding to the point when the gradient of $P_{aw}$ changes is determined, as illustrated in FIG. 12.

In operation 162, a difference or ratio is calculated between the lowest level of EAdi and the EAdi level corresponding to a change in gradient of $P_{aw}$. As mentioned hereinabove, this difference or ratio allows to express the amount of absolute or relative increase in EAdi contributed by the respiratory mechanical load. The difference or ratio in EAdi can be calculated through a calculator (not shown), for example.

Therefore, the amount of absolute or relative increase in EAdi allows for quantification of respiratory drive and partition of the respiratory drive into chemical/habitual drive and load related drive.

Although the present invention has been described in the foregoing disclosure in connection with a non-restrictive illustrative embodiment thereof, various modification to this embodiment can be made within the scope of the appended claims without departing from the spirit and nature of the present invention.

What is claimed is:

1. A method for determining dynamically a respiratory feature in a spontaneously breathing patient receiving mechanical ventilatory assist, the method comprising:
   using a respiratory neural drive detector to measure a respiratory neural drive of the spontaneously breathing patient;
   using a neurally controlled ventilator to apply ventilatory assist pressure to the spontaneously breathing patient as a function of the respiratory neural drive of the spontaneously breathing patient;
   using a controller to modify a level of mechanical ventilatory assist applied to the spontaneously breathing patient by the neurally controlled ventilator until an airway pressure detector detects a change of gradient of a measured airway pressure of the spontaneously breathing patient, wherein the gradient represents a rate of change for the measured airway pressure in response to modifying the level of mechanical ventilatory assist; and
   determining, using a calculator, the respiratory feature of the spontaneously breathing patient based on the measured airway pressure upon detecting the change of gradient of the airway pressure.

2. A method as defined in claim 1, wherein modifying the level of mechanical ventilatory assist to the spontaneously breathing patient comprises increasing, using the controller, the level of mechanical ventilatory assist to the spontaneously breathing patient.

3. A method as defined in claim 1, wherein modifying the level of mechanical ventilatory assist to the spontaneously breathing patient further comprises decreasing, using the controller, the level of mechanical ventilatory assist to the spontaneously breathing patient.

4. A method as defined in claim 1, wherein modifying the level of mechanical ventilatory assist to the spontaneously breathing patient comprises using, in the controller, a proportionality factor.

5. A method as defined in claim 4, wherein modifying the level of mechanical ventilatory assist to the spontaneously breathing patient comprises modifying, using the controller, the proportionality factor in a linear manner.

6. A method as defined in claim 4, wherein modifying the level of mechanical ventilatory assist to the spontaneously breathing patient further comprises modifying, using the controller, the proportionality factor in a non-linear manner.

7. A method as defined in claim 4, wherein modifying the level of mechanical ventilatory assist to the spontaneously breathing patient further comprises modifying, using the controller, the proportionality factor in an arbitrary manner.

8. A method as defined in claim 1, further comprising using, in the calculator, the measured airway pressure upon detecting the change of gradient of the measured airway pressure to physiologically determine respiratory muscle unloading.

9. A method as defined in claim 1, wherein detecting a change of gradient of the airway pressure comprises detecting, in the calculator, a plateau of the airway pressure.

10. A method as defined in claim 1, wherein the measured airway pressure is proportional to the respiratory neural drive.

11. A method as defined in claim 1, wherein the respiratory neural drive is an electrical activity of the patient's diaphragm (EAdi).

12. A method for determining dynamically a respiratory feature in a spontaneously breathing patient receiving mechanical ventilatory assist, the method comprising:
    using a respiratory neural drive detector to measure a respiratory neural drive of the spontaneously breathing patient;
    using a neurally controlled ventilator to apply ventilatory assist pressure to the spontaneously breathing patient as a function of the respiratory neural drive of the spontaneously breathing patient;
    using a cntroller to modify a level of mechanical ventilatory assist applied to the spontaneously breathing patient by the neurally controlled ventilator until a lowest level of the measured respiratory neural drive is detected; and
    determining, using a calculator, the respiratory feature of the spontaneously breathing patient based on the level of mechanical ventilatory assist when the detected respiratory neural drive is at the lowest level.

13. A method as defined in claim 12, wherein modifying the level of mechanical ventilatory assist to the spontaneously breathing patient comprises increasing, using the controller, the level of mechanical ventilatory assist to the spontaneously breathing patient.

14. A method as defined in claim 12, wherein modifying the level of mechanical ventilatory assist to the spontaneously breathing patient comprises using, in the controller, a proportionality factor.

15. A method as defined in claim 14, wherein modifying the level of mechanical ventilatory assist to the spontaneously breathing patient comprises modifying, using the controller, the proportionality factor in a linear manner.

16. A method as defined in claim 14, wherein modifying the level of mechanical ventilatory assist to the spontaneously breathing patient further comprises modifying, using the controller, the proportionality factor in a non-linear manner.

17. A method as defined in claim 14, wherein modifying the level of mechanical ventilatory assist to the spontaneously breathing patient further comprises modifying, using the controller, the proportionality factor in an arbitrary manner.

18. A method as defined in claim 12, wherein the respiratory feature comprises elastance of a lung.

19. A method as defined in claim 12, wherein the respiratory feature comprises resistance of a lung.

20. A method as defined in claim 12, further comprising measuring, using an airway pressure detector, an airway pressure corresponding to the detected lowest level of respiratory neural drive.

21. A method as defined in claim 20, wherein the measured airway pressure corresponding to the detected lowest level of respiratory neural drive represents a transpulmonary pressure required for distending lungs.

22. A method as defined in claim 21, wherein determining the respiratory feature based on the detected lowest level of respiratory neural drive comprises calculating, using the calculator, the respiratory feature using the transpulmonary pressure.

23. A method as defined in claim 12, wherein the respiratory neural drive is an electrical activity of the spontaneously breathing patient's diaphragm (EAdi).

24. A method as defined in claim 12, wherein detecting a lowest, level of respiratory neural drive comprises detecting, using the neural drive detector, a plateau of the respiratory neural drive.

25. A method as defined in claim 12, further comprising applying, using an expiratory valve, at least one level of positive end-expiratory pressure (PEEP) at the detected lowest level of respiratory neural drive so as to determine a level of PEEP associated with a least impaired respiratory feature.

26. A method as defined in claim 12, further comprising measuring an airway pressure and detecting a change of gradient of the measured airway pressure, using an airway pressure detector.

27. A method as defined in claim 26, further comprising determining, using a second calculator, an amount of respiratory neural drive contributed by respiratory mechanical load.

28. A method as defined in claim 27, wherein determining an amount of respiratory neural drive contributed by respiratory mechanical load comprises calculating, using the second calculator, a difference in the respiratory neural drive between a lowest level of respiratory neural drive and a level of respiratory neural drive at the change of gradient of the measured airway pressure.

29. A method as defined in claim 27, wherein determining an amount of respiratory neural drive contributed by respiratory mechanical load comprises calculating, using the second calculator, a ratio of the respiratory neural drive between a lowest level of respiratory neural drive and a level of respiratory neural drive at the change of gradient of the measured airway pressure.

30. A device for determining dynamically a respiratory feature in a spontaneously breathing patient receiving mechanical ventilatory assist, the device comprising:
a respiratory neural drive detector for measuring a respiratory neural drive of the spontaneously breathing patient;
a neurally controlled ventilator for applying ventilatory assist pressure to the spontaneously breathing patient as a function of the respiratory neural drive of the spontaneously breathing patient;
a controller of the neurally controlled ventilator for modifying a level of mechanical ventilatory assist to the spontaneously breathing patient until an airway pressure detector detects a change of gradient of a measured airway pressure of the spontaneously breathing patient, wherein the gradient represents a rate of change of the measured airway pressure in response to modifying the level of mechanical ventilatory assist; and
a calculator, connected to the airway pressure detector, for determining the respiratory feature of the spontaneously breathing patient based on the airway pressure measured upon detecting the change of gradient of the measured airway pressure.

31. A device as defined in claim 30, wherein the controller modifies the level of mechanical ventilatory assist to the spontaneously breathing patient by increasing said level of mechanical ventilatory assist.

32. A device as defined in claim 30, wherein the controller modifies the level of mechanical ventilatory assist to the spontaneously breathing patient by decreasing said level of mechanical ventilatory assist.

33. A device as defined in claim 30, wherein the controller comprises a proportionality factor for modifying the level of mechanical ventilatory assist to the spontaneously breathing patient.

34. A device as defined in claim 33, wherein the controller changes the proportionality factor in relation to a linear function for modifying the level of mechanical ventilatory assist to the spontaneously breathing patient.

35. A device as defined in claim 33, wherein the controller changes the proportionality factor in relation to a non-linear function for modifying the level of mechanical ventilatory assist to the spontaneously breathing patient.

36. A device as defined in claim 33, wherein the controller changes the proportionality factor in relation to an arbitrary function for modifying the level of mechanical ventilatory assist to the spontaneously breathing patient.

37. A device as defined in claim 33, wherein the calculator uses the measured airway pressure upon detecting the change of gradient of the measured airway pressure to physiologically determine respiratory muscle unloading.

38. A device as defined in claim 30, wherein the airway pressure detector detects a plateau reached by the airway pressure.

39. A device as defined in claim 30, wherein the airway pressure detector measures an airway pressure which is proportional to the respiratory neural drive.

40. A device as defined in claim 30, wherein the respiratory neural drive is an electrical activity of the patient's diaphragm (EAdi).

41. A device for determining dynamically a respiratory feature in a spontaneously breathing patient receiving mechanical ventilatory assist, the device comprising:
a respiratory neural drive detector for measuring a respiratory neural drive of the spontaneously breathing patient;
a neurally controlled ventilator for applying ventilatory assist pressure to the spontaneously breathing patient as a function of the respiratory neural drive of the spontaneously breathing patient;
a controller of the neurally controlled ventilator for modifying a level of mechanical ventilatory assist to the spontaneously breathing patient until a lowest level of the measured respiratory neural drive is detected; and
a calculator for determining the respiratory feature of the spontaneously breathing patient based on the level of mechanical ventilatory assist when the detected respiratory neural drive is at the lowest level.

42. A device as defined in claim 41, wherein the controller comprises a proportionality factor for modifying the level of mechanical ventilatory assist to the spontaneously breathing patient.

43. A device as defined in claim 42, wherein the controller changes the proportionality factor in relation to a linear function for modifying the level of mechanical ventilatory assist to the spontaneously breathing patient.

44. A device as defined in claim 42, wherein the controller changes the proportionality factor in relation to a non-linear function for modifying the level of mechanical ventilatory assist to the spontaneously breathing patient.

45. A device as defined in claim 42, wherein the controller changes the proportionality factor in relation to an arbitrary function for modifying the level of mechanical ventilatory assist to the spontaneously breathing patient.

46. A device as defined in claim 41, wherein the respiratory feature comprises elastance of a lung.

47. A device as defined in claim 41, wherein the respiratory feature comprises resistance of a lung.

48. A device as defined in claim 41, further comprising an airway pressure detector for measuring an airway pressure corresponding to the detected lowest level of the measured respiratory neural drive.

49. A device as defined in claim 48, wherein the measured airway pressure corresponding to the detected lowest level of the measured respiratory neural drive represents a transpulmonary pressure for distending lungs.

50. A device as defined in claim 49, wherein the calculator uses the measured airway pressure corresponding to the detected lowest level of the measured respiratory neural drive for determining the respiratory feature.

51. A device as defined in claim 41, wherein the respiratory neural drive is an electrical activity of the spontaneously breathing patient's diaphragm (EAdi).

52. A device as defined in claim 41, wherein the respiratory neural drive detector detects a plateau of the respiratory neural drive.

53. A device as defined in claim 41, further comprising a PEEP supplier for applying a level of PEEP at the detected lowest level of respiratory neural drive so as to determine a level of PEEP associated with a least impaired respiratory feature.

54. A device as defined in claim 41, further comprising an airway pressure detector for measuring an airway pressure and detecting a change of gradient of the measured airway pressure.

55. A device as defined in claim 54, wherein the calculator determines an amount of respiratory neural drive contributed by respiratory mechanical load.

56. A device as defined in claim 55, wherein the calculator determines the amount of respiratory neural drive contributed by respiratory mechanical load by determining a difference in the respiratory neural drive between a lowest level of the measured respiratory neural drive and a level of respiratory neural drive at the change of gradient of the measured airway pressure.

57. A device as defined in claim 55, wherein the calculator determines the amount of respiratory neural drive contributed by respiratory mechanical load by determining a ratio between a lowest level of the measured respiratory neural drive and a level of respiratory neural drive at the change of gradient of the measured airway pressure.

* * * * *